(12) United States Patent
Wong et al.

(10) Patent No.: US 9,115,119 B2
(45) Date of Patent: Aug. 25, 2015

(54) ELECTRON TRANSPORT MATERIAL AND ORGANIC LIGHT EMITTING DEVICE

(75) Inventors: Ken-Tsung Wong, New Taipei (TW); Hsiao-Fan Chen, New Taipei (TW); Ting-Chih Wang, Taipei (TW); Shih-Wei Lin, Taitung County (TW); Wen-Yi Hung, New Taipei (TW); Qu-Yuan Liu, Taoyuan County (TW); Meng-Huan Ho, Taipei (TW); Ting-Yi Cho, New Taipei (TW); Chieh-Wei Chen, Taichung (TW); Chung-Chun Lee, Hsinchu (TW)

(73) Assignee: Au Optronics Corporation, Hsinchu (TW)

( * ) Notice: Subject to any disclaimer, the term of this patent is extended or adjusted under 35 U.S.C. 154(b) by 574 days.

(21) Appl. No.: 13/445,920

(22) Filed: Apr. 13, 2012

(65) Prior Publication Data

US 2013/0153863 A1   Jun. 20, 2013

(30) Foreign Application Priority Data

Dec. 19, 2011  (TW) .............. 100147202 A

(51) Int. Cl.
*H01L 51/50* (2006.01)
*C07D 403/14* (2006.01)
*H01L 51/00* (2006.01)

(52) U.S. Cl.
CPC .......... *C07D 403/14* (2013.01); *H01L 51/0067* (2013.01); *H01L 51/5072* (2013.01)

(58) Field of Classification Search
None
See application file for complete search history.

(56) References Cited

U.S. PATENT DOCUMENTS 6,057,048 A   5/2000 Hu et al.
6,225,467 B1  5/2001 Esteghamatian et al.
(Continued)

FOREIGN PATENT DOCUMENTS

JP   2004-022334   *  1/2004  ............. C09K 11/06

OTHER PUBLICATIONS

Huang et al., 7-Azaindolyl- and indolyl-functionalized starburst molecules with a 1, 3, 5-triazine or benzene core-Syntheses and luminescent, 2006, Can. J. Chem., vol. 84, pp. 477-485.*
Zheng et al., "Assembly of CdI2-type coordination networks from triangular ligand and octahedral metal center: topological analysis and potential framework porosity", Chemical Communications 2008(3), 2008, 356-358, Abstract available at http://ukpmc.ac.uk/abstract/med/18399206/.
Li et al., "Design and Synthesis of Polypyrazolyl Compounds as a New Type of Versatile Building Blocks", Chin. J. Chem. 24(09), 2006, 1225-1229, Abstract available at http://sioc-journal.cn/Jwk_z ghx/CN/abstract/abstract336748.shtml.
Comparative Toxicogenomics Database (CTD), http://ctd.mdibl.org/detail.go?type=chem&acc=C526989#top.

*Primary Examiner* — Gregory Clark
(74) *Attorney, Agent, or Firm* — Jianq Chyun IP Office

(57) ABSTRACT

An organic light emitting device is provided. The organic light emitting device includes a first electrode layer, a second electrode layer and a light emitting material layer. The second electrode layer is disposed opposite to the first electrode layer. The light emitting material layer is disposed between the first electrode layer and the second electrode layer, and includes an organic light emitting material and an electron transport material, wherein the electron transport material includes a compound represented by a formula (1) below:

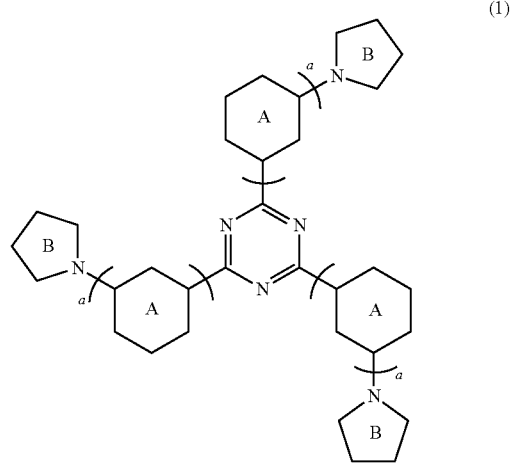

in which a group A represents an aromatic ring, a is 1, and a group B represents a nitrogen containing five-membered heterocyclic group and derivatives thereof, and has at least one nitrogen atom connected to a meta-position of the group A.

14 Claims, 2 Drawing Sheets

(56) References Cited

U.S. PATENT DOCUMENTS

| | | |
|---|---|---|
| 6,229,012 B1 | 5/2001 | Hu et al. |
| 2007/0018569 A1* | 1/2007 | Kawamura et al. ........... 313/504 |
| 2007/0141390 A1 | 6/2007 | Coggan et al. |
| 2009/0162764 A1 | 6/2009 | Wu et al. |
| 2010/0184942 A1 | 7/2010 | Chen et al. |
| 2011/0095282 A1 | 4/2011 | Pflumm et al. |
| 2011/0108823 A1 | 5/2011 | Stoessel et al. |
| 2011/0190494 A1 | 8/2011 | Aihara et al. |

* cited by examiner

ELECTRON TRANSPORT MATERIAL AND ORGANIC LIGHT EMITTING DEVICE

CROSS-REFERENCE TO RELATED APPLICATION

This application claims the priority benefit of Taiwan application serial no. 100147202, filed on Dec. 19, 2011. The entirety of the above-mentioned patent application is hereby incorporated by reference herein and made a part of this specification.

BACKGROUND OF THE INVENTION

1. Field of the Invention

The present invention relates to a material and a device, and more particularly to an electron transport material and an organic light emitting device.

2. Description of Related Art

With the development of science and technology, a flat panel display is the most focused display technology in recent years. An organic electroluminescent display is self-luminous, viewing-angle independent, power saving, simple in fabrication, and has a low cost, a low temperature operating range, a high response speed, and the full color. With these advantages, the organic electroluminescent display has a great potential in applications and might become the mainstream of the next generation flat panel displays.

The organic light emitting device includes an anode, an organic light emitting layer, and a cathode. The luminescence mechanism of the organic light emitting device is to inject a hole and an electron from the anode and the cathode to the organic light emitting layer, respectively. When the electron and the hole meet in the organic light emitting layer and recombine to form an exciton, so as to generate the phenomenon of light emission to emit a photon. Generally speaking, for an organic material, the conduction velocity of the electron is much smaller than the conduction velocity of the hole. Due to such a characteristic, the charge recombination region is close to the cathode and the probability of exciton quenching is increased.

To reach the balance between the electron and the hole in terms of the transport to facilitate that the exciton recombination region is located in the organic light emitting layer, in the organic light emitting device, an electron transport layer (ETL) including a material having a high electron transport velocity is usually disposed between the organic light emitting layer and the cathode. Generally speaking, the electron transport material needs to have the characteristics such as a suitable lowest unoccupied molecular orbital (LUMO) energy level, a high electron transport velocity, and a high glass transition temperature and thermal stability. As a triazine is a typical electron-poor heterocyclic system and has a high electron affinity, a desirable electron conduction velocity, and a simple synthesis method, for example, the 1,3,5-triazine derivative is widely used as the electron conduction material.

However, the current known 1,3,5-triazine derivative has a high LUMO energy level of about −1.93 eV to −2.08 eV, resulting in a large energy barrier when the electron is injected to the ETL from the cathode, thereby further affecting an initial voltage and an operating voltage of the device. Therefore, a proper electron transport material urgently needs to be developed in this field.

SUMMARY OF THE INVENTION

The present invention provides an organic light emitting device, which has a desirable luminous efficiency.

The present invention further provides an electron transport material, which has a relatively low LUMO energy level.

The present invention provides an organic light emitting device, which includes a first electrode layer, a second electrode layer, and a light emitting material layer. The second electrode layer is disposed opposite to the first electrode layer. The light emitting material layer is disposed between the first electrode layer and the second electrode layer and includes an organic light emitting material and an electron transport material. The electron transport material includes a compound represented by a formula (1) below:

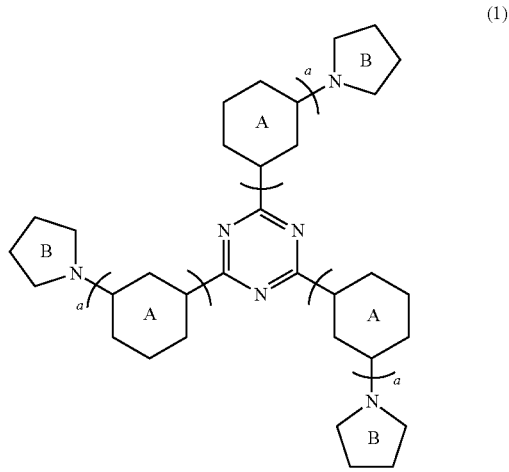

(1)

in which a group A represents an aromatic ring, a is 1, and a group B represents a nitrogen containing five-membered heterocyclic group and derivatives thereof, and has at least one nitrogen atom connected to a meta-position of the group A.

The present invention further provides an electron transport material, applicable to an organic light emitting device, and the electron transport material includes a compound represented by a formula (1) below:

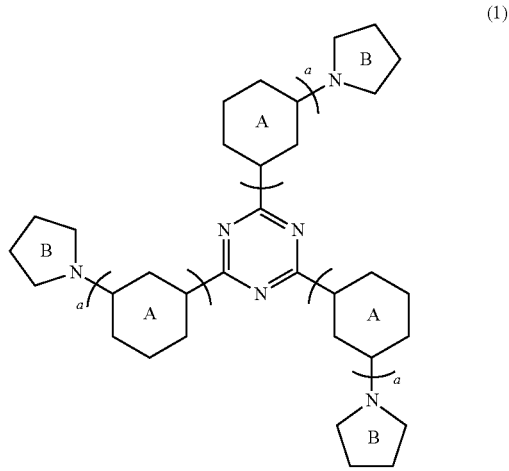

(1)

in which a group A represents an aromatic ring, a is 1, and a group B represents a nitrogen containing five-membered heterocyclic group and derivatives thereof, and has at least one nitrogen atom connected to a meta-position of the group A.

The present invention further provides an electron transport material, applicable to an organic light emitting device, and the electron transport material includes a compound represented by a formula (6) below:

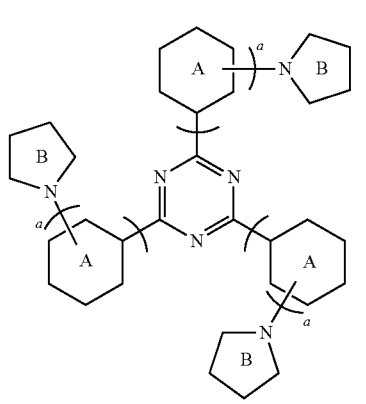

(6)

in which a group A represents an aromatic ring, a is 1, and a group B represents a nitrogen containing five-membered heterocyclic group and derivatives thereof, and has at least one nitrogen atom connected to a position other than the opposite position of the group A.

Based on the above, the present invention provides an electron transport material, which has a relatively low LUMO energy level. Therefore, when the electron transport material is used in the organic light emitting device, the energy barrier of injecting the electron can be reduced, so as to enhance the luminous efficiency of the organic light emitting device.

In order to make the aforementioned and other objectives and advantages of the present invention comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
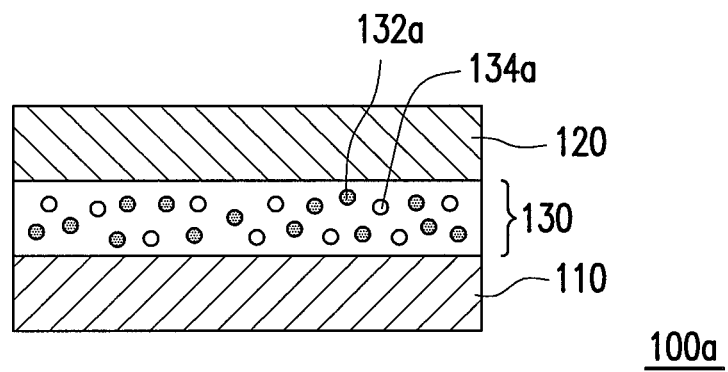
FIG. 1A is a schematic sectional view of an organic light emitting device according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

The present invention provides an electron transport material, applicable to an organic light emitting device, and the electron transport material includes a compound represented by a formula (1) below:

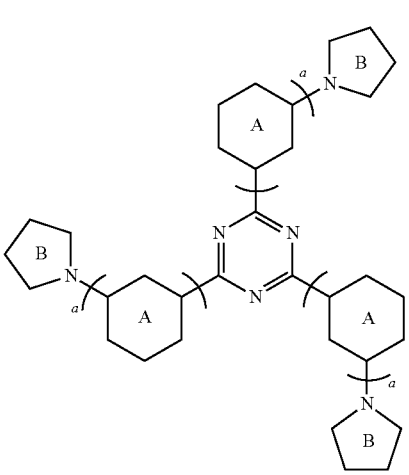

(1)

in which a group A represents an aromatic ring, a is 1, and a group B represents a nitrogen containing five-membered heterocyclic group and derivatives thereof, and has at least one nitrogen atom connected to a meta-position of the group A.

In particular, the compound of the formula (1) uses a 1,3,5-triazine as the core molecule and positions 2,4,6 of the triazine are substituted by the group A. A nitrogen containing group B is introduced at a meta-position of the group A. For the meta-position of the group A here, a position where the group A is connected to the core structure 1,3,5-triazine is used as a reference, an opposite position of the group A is the position opposite the reference position, and the meta-position of the group A is the position adjacent to the opposite position. For example, when the group A is a benzene ring, the group B is connected to the meta-position of the group A (referring to a formula (2)). That is to say, when a position 1 of the group A is connected to the core structure 1,3,5-triazine, the group B is connected to a position 3 or 5 of the group A. When the group A is a naphthalene ring, a position 2 of the group A is connected to the core structure 1,3,5-triazine, and the group B can be connected to a position 7 of the group A (referring to a formula (3)), or connected to a position 4 or 5 of the group A, and so on. In an embodiment, preferably, the manner that the group A and the group B are connected is exemplarily the bonding of a carbon-nitrogen (C—N) bond. Such bonding can provide the group A and the group B with a desirable electron transport capability, which can enhance the electron transport capability of the whole compound more than the bonding of a carbon-carbon (C—C) bond.

In an embodiment, the group A is an aromatic ring, which can be a six-membered ring, or another many-membered ring (for example, a five-membered ring), or a derivative thereof. For example, the aromatic ring also can be a fused ring, a bridge-fused ring, or a derivative fused ring having another substituent functional group. In an embodiment, the group A represents, for example, a benzene ring, a fused benzene ring, a bridge-fused benzene ring, a derivative or a similar group thereof. The fused benzene ring can be such as an oligo-acene ring or a poly-acence ring, and the bridge-fused benzene ring can be such as an oligo-p-phenylene ring or a poly-p-phenylene ring. In an embodiment, the group A represents, for example, a benzene ring, a naphthalene ring, a biphenyl ring, a derivative or a similar group thereof.

In an embodiment, the group B is, for example, an electron withdrawing group. In an embodiment, the group B is selected from the group consisting of:

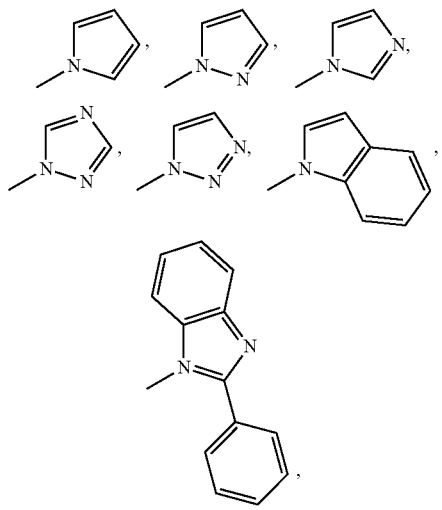

and derivatives and similar groups thereof.

In an embodiment, the LUMO energy level of the electron transport material is, for example, between −2.6 eV and −3.0 eV.

In an embodiment, the group A represents, for example, a benzene ring. The electron transport material includes, for example, a compound represented by a formula (2) below:

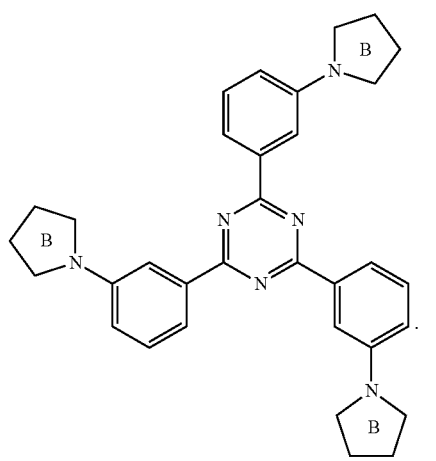

(2)

The group B in the compound of the formula (2) is, for example, an electron withdrawing group. The group B in the compound of the formula (2) is, for example, selected from the group consisting of

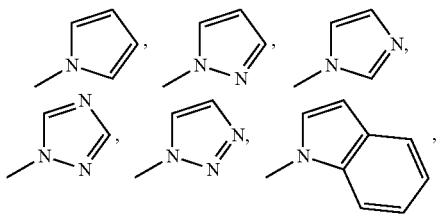

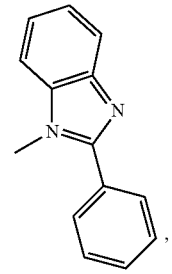

and derivatives and similar groups thereof. Therefore, the compound of the formula (2) is, for example, 2,4,6-tris(3-(1H-pyrrol-1-yl)phenyl)-1,3,5-triazine (TPT-01), 2,4,6-tris(3-(1H-pyrazol-1-yl)phenyl)-1,3,5-triazine (TPT-02), 2,4,6-tris(3-(1H-imidazol-1-yl)phenyl)-1,3,5-triazine (TPT-03), 2,4,6-tris(3-(1H-1,2,3-triazol-1-yl)phenyl)-1,3,5-triazine (TPT-04), 2,4,6-tris(3-(1H-1,2,4-triazol-1-yl)phenyl)-1,3,5-triazine (TPT-05), 2,4,6-tris(3-(1H-indol-1-yl)phenyl)-1,3,5-triazine (TPT-06), 2,4,6-tris(3-(2-phenyl-1H-benzo[d]imidazol-2-yl)phenyl)-1,3,5-triazine (TPT-07), a derivative or a similar group thereof.

(TPT-01)

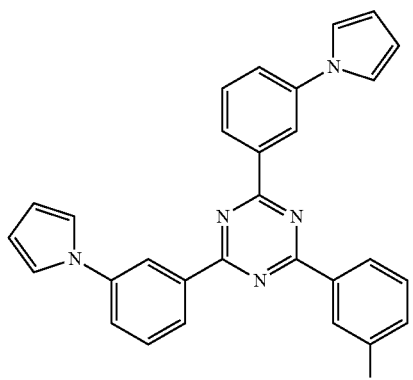

(TPT-02)

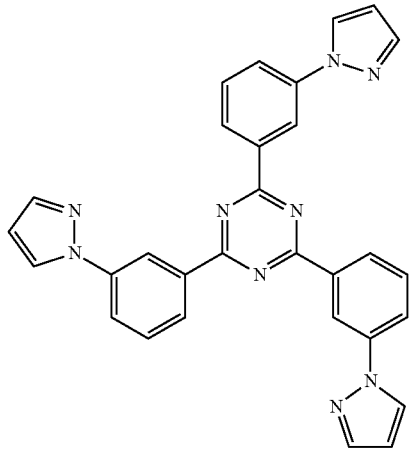

(TPT-03)
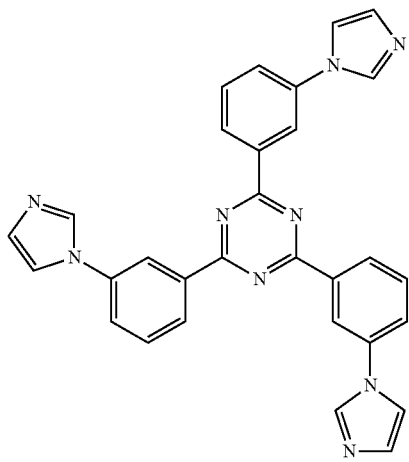
(TPT-04)
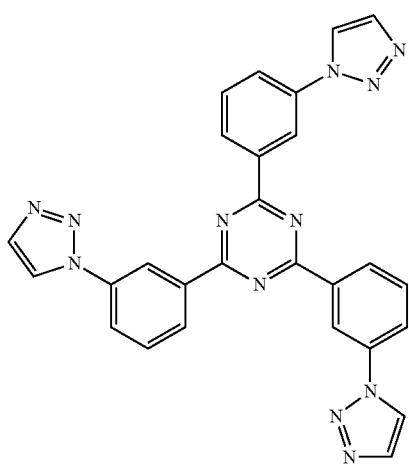
(TPT-05)
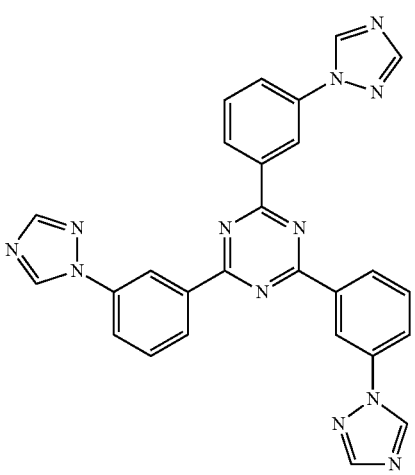
(TPT-06)
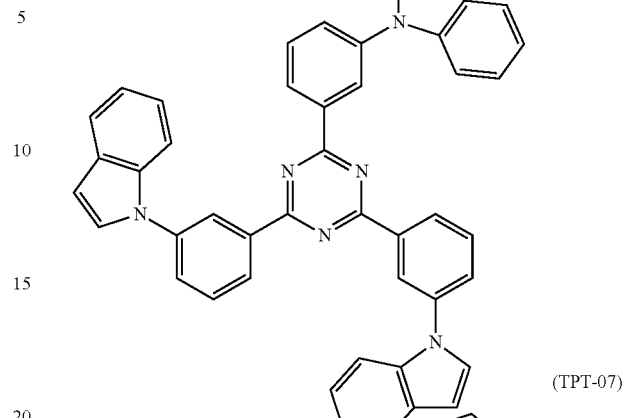
(TPT-07)
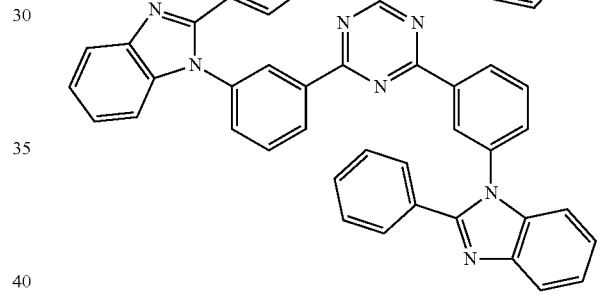
In an embodiment, the group A represents, for example, a naphthalene ring. The electron transport material includes, for example, a compound represented by a formula (3) below:
(3)
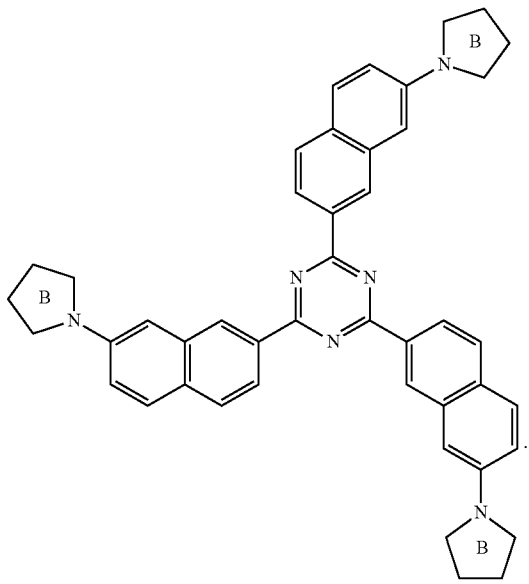

The group B in the compound of the formula (3) is, for example, an electron withdrawing group. The group B in the compound of the formula (3) is, for example, selected from the group consisting of:

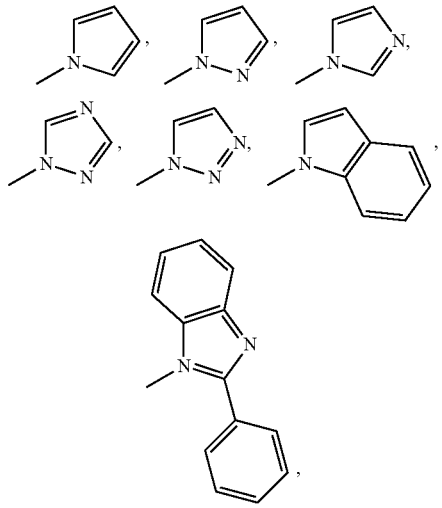

and derivatives and similar groups thereof. Therefore, the compound of the formula (3) is, for example, 2,4,6-tris(7-(1H-pyrrol-1-yl)naphthalen-2-yl)-1,3,5-triazine (TNT-01), 2,4,6-tris(7-(1H-pyrazol-1-yl)naphthalen-2-yl)-1,3,5-triazine (TNT-02), 2,4,6-tris(7-(1H-imidazol-1-yl)naphthalen-2-yl)-1,3,5-triazine (TNT-03), 2,4,6-tris(7-(1H-1,2,3-triazol-1-yl)naphthalen-2-yl)-1,3,5-triazine (TNT-04), 2,4,6-tris(7-(1H-1,2,4-triazol-1-yl)naphthalen-2-yl)-1,3,5-triazine (TNT-05), 2,4,6-tris(7-(1H-indol-1-yl)naphthalen-2-yl)-1,3,5-triazine (TNT-06), 2,4,6-tris(7-(2-phenyl-1H-benzo[d]imidazol-2-yl)naphthalen-2-yl)-1,3,5-triazine (TNT-07), a derivative thereof or a similar group thereof.

(TNT-02)

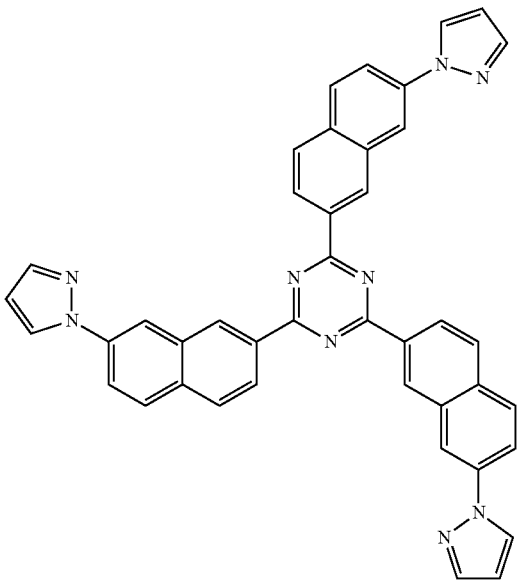

(TNT-01)

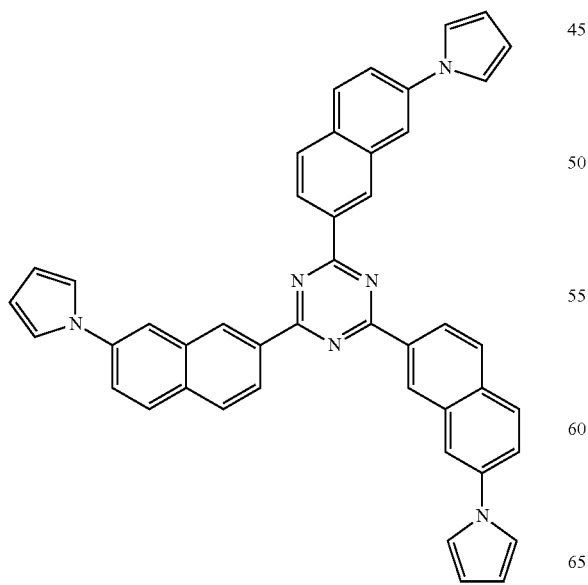

(TNT-03)

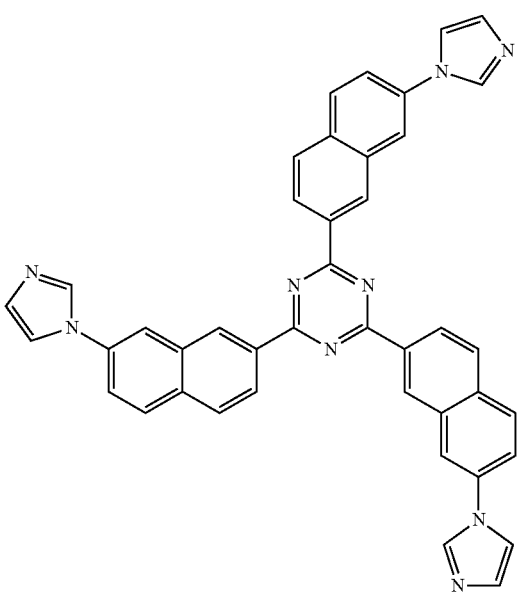

-continued
(TNT-04)
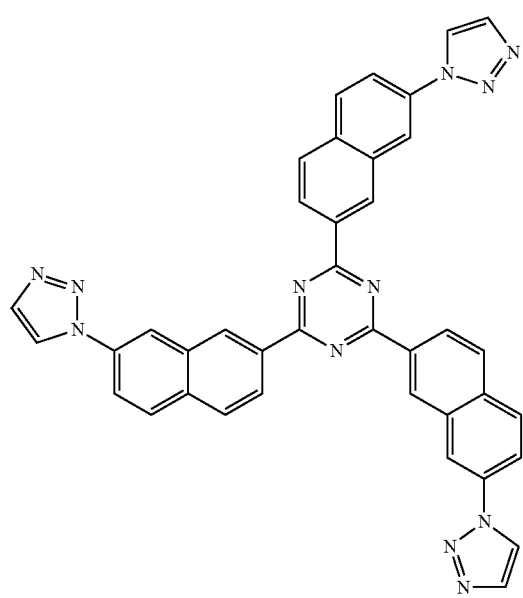
(TNT-06)
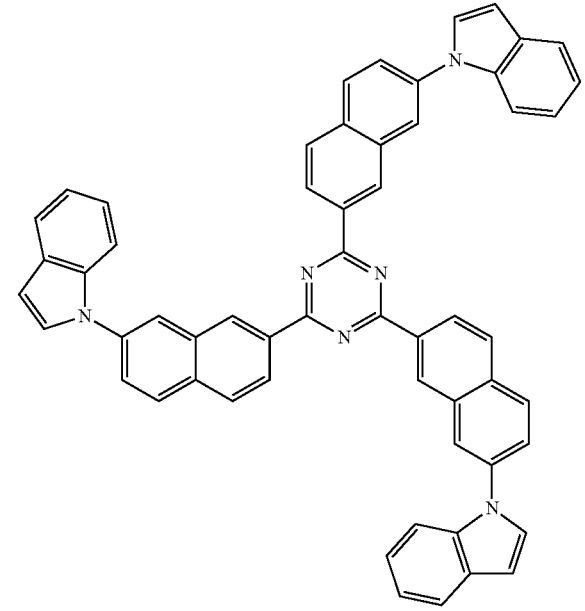
(TNT-05)
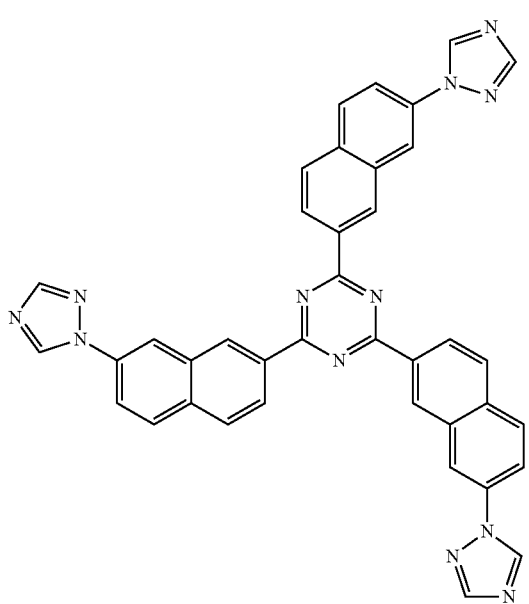
(TNT-07)
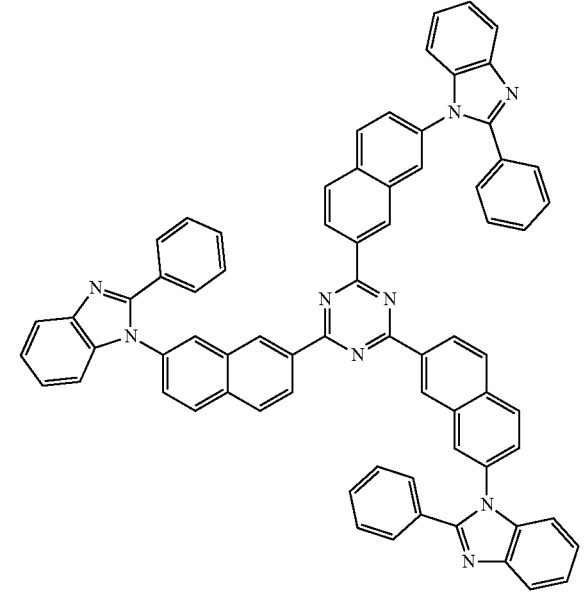
In an embodiment, the group A represents, for example, a biphenyl ring. The electron transport material includes, for example, a compound represented by a formula (4) below:

(4)

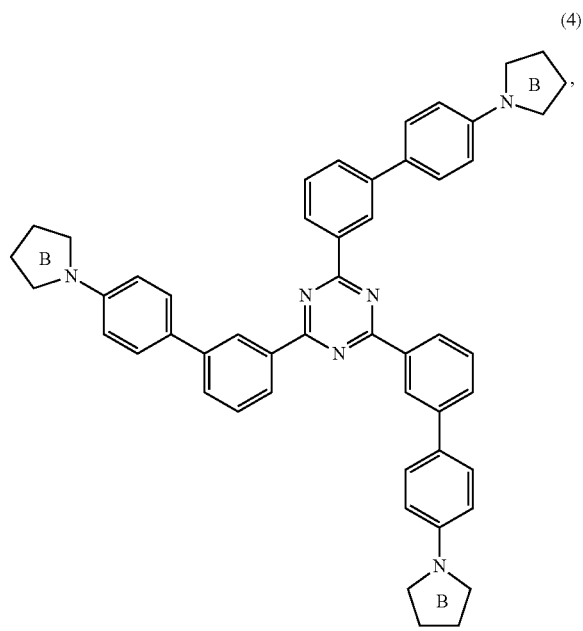

The group B in the compound of the formula (4) is, for example, an electron withdrawing group. The group B in the compound of the formula (4) is, for example, selected from the group consisting of:

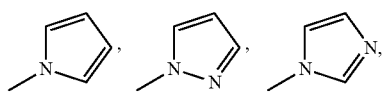

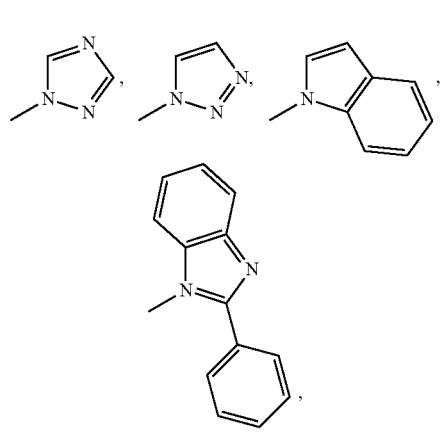

and derivatives or similar groups thereof. Therefore, the compound of the formula (4) is, for example, 2,4,6-tris(4'-(1H-pyrrol-1-yl)biphenyl-3-yl)-1,3,5-triazine (TBT-01), 2,4,6-tris(4'-(1H-pyrazol-1-yl)biphenyl-3-yl)-1,3,5-triazine (TBT-02), 2,4,6-tris(4'-(1H-imidazol-1-yl)biphenyl-3-yl)-1,3,5-triazine (TBT-03), 2,4,6-tris(4'-(1H-1,2,3-triazol-1-yl)biphenyl-3-yl)-1,3,5-triazine (TBT-04), 2,4,6-tris(4'-(1H-1,2,4-triazol-1-yl)biphenyl-3-yl)-1,3,5-triazine (TBT-05), 2,4,6-tris(4'-(1H-indol-1-yl)biphenyl-3-yl)-1,3,5-triazine (TBT-06), 2,4,6-tris(4'-(2-phenyl-1H-benzo[d]imidazol-1-yl)biphenyl-3-yl)-1,3,5-triazine (TBT-07), a derivative or a similar group thereof.

(TBT-01)

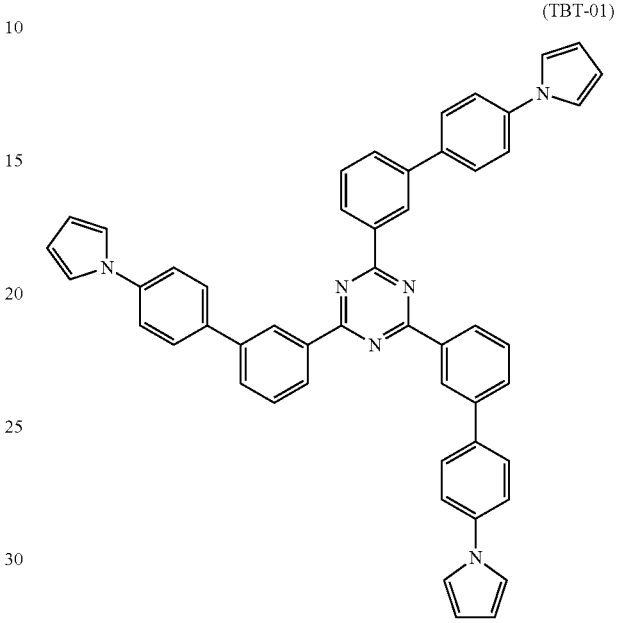

(TBT-02)

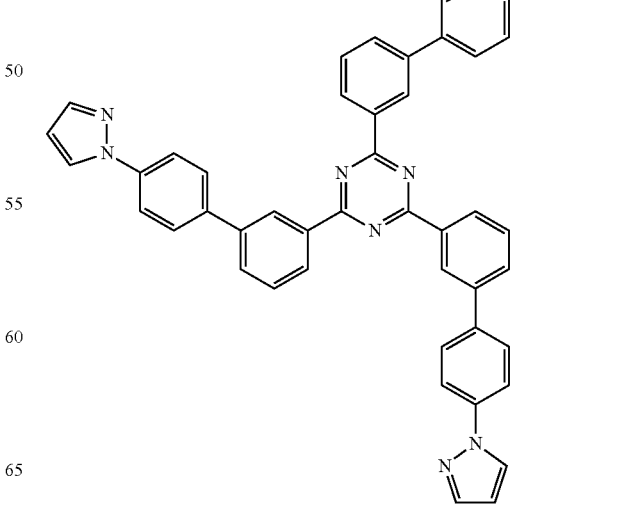

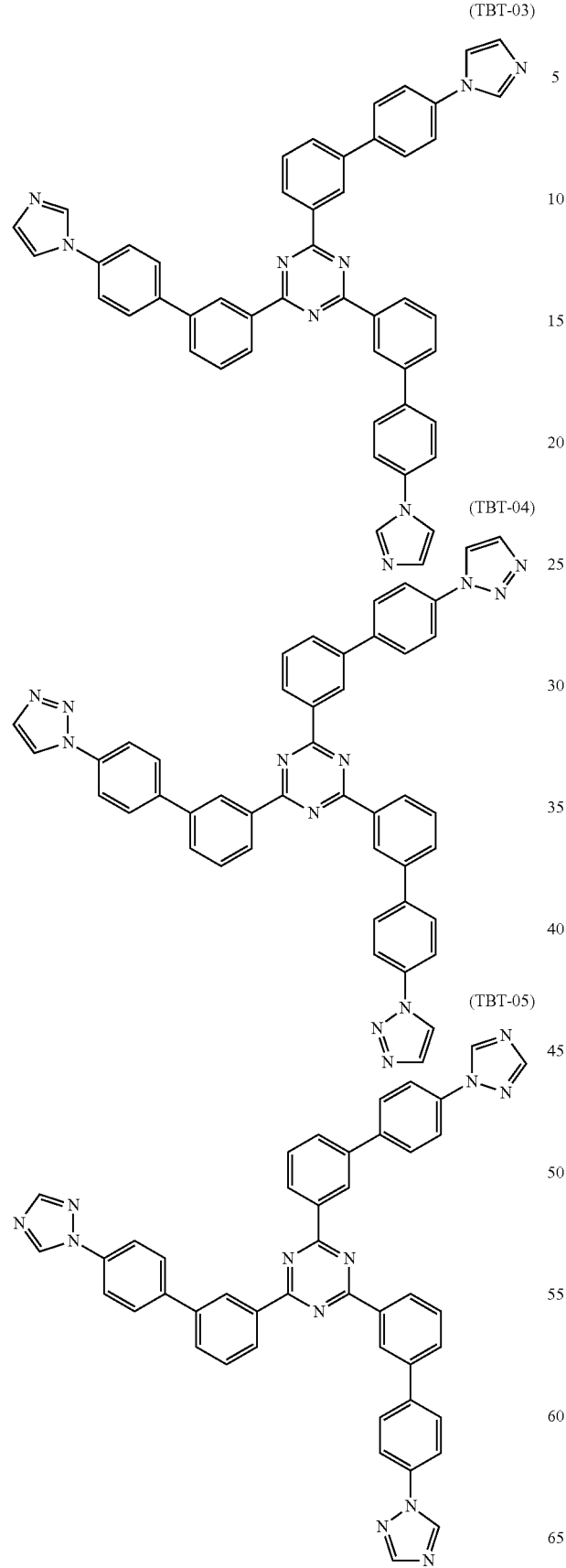
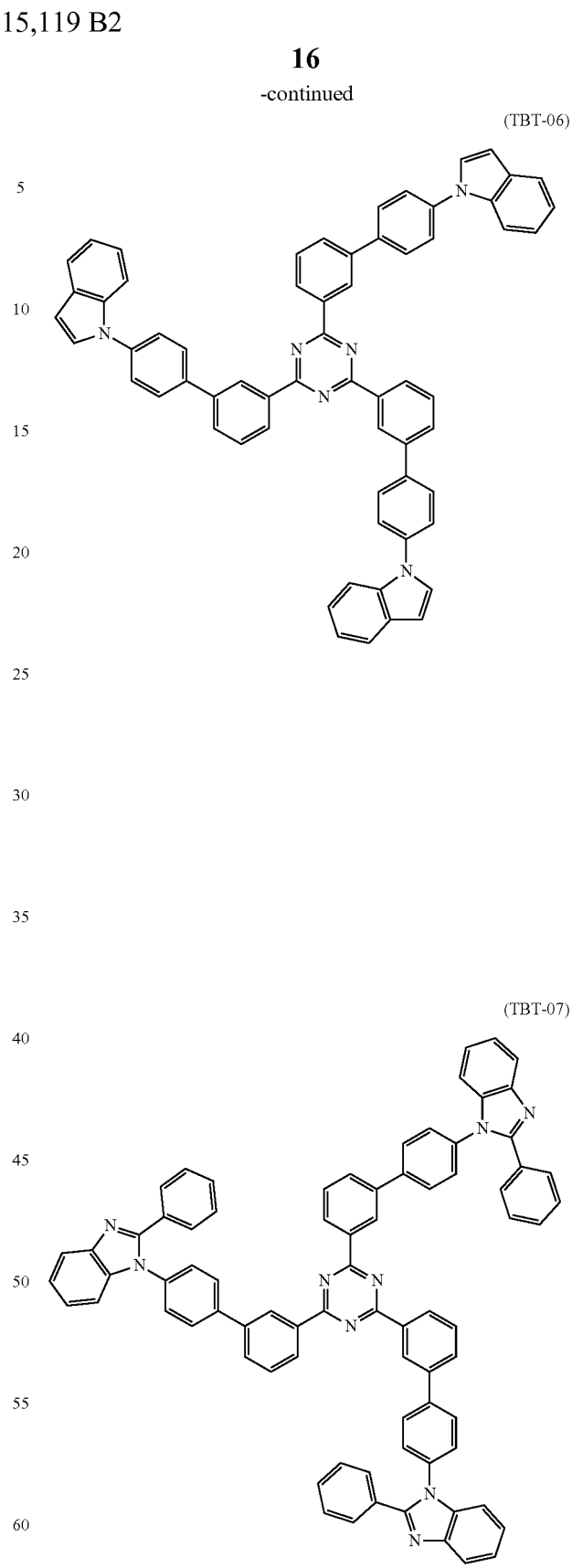
In an embodiment, the group A represents, for example, a biphenyl ring. The electron transport material includes, for example, a compound represented by a formula (5) below:

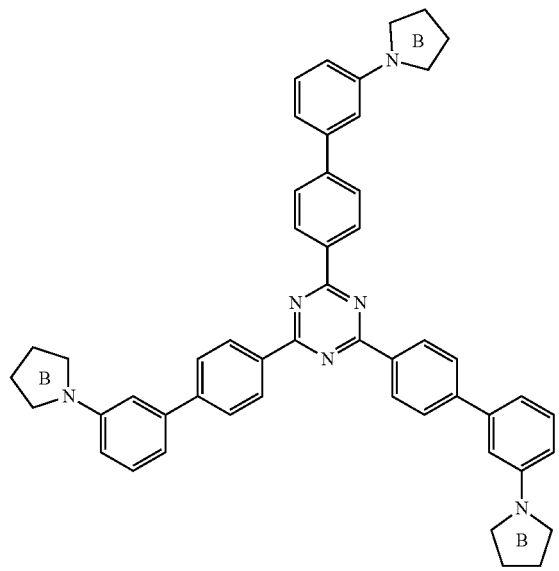
(5)

The group B in the compound of the formula (5) is, for example, an electron withdrawing group. The group B in the compound of the formula (5) is, for example, selected from the group consisting of:

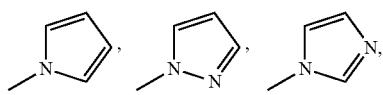

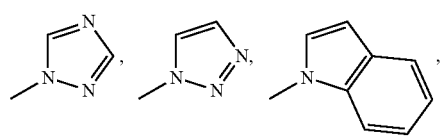

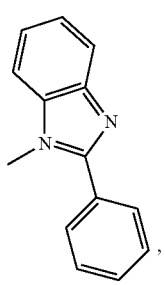

and derivatives and similar groups thereof. Therefore, the compound of the formula (5) is, for example, 2,4,6-tris(3'-(1H-pyrrol-1-yl)biphenyl-4-yl)-1,3,5-triazine (TBT-08), 2,4,6-tris(3'-(1H-pyrazol-1-yl)biphenyl-4-yl)-1,3,5-triazine (TBT-09), 2,4,6-tris(3'-(1H-imidazol-1-yl)biphenyl-4-yl)-1,3,5-triazine (TBT-10), 2,4,6-tris(3'-(1H-1,2,3-triazol-1-yl)biphenyl-4-yl)-1,3,5-triazine (TBT-11), 2,4,6-tris(3'-(1H-1,2,4-triazol-1-yl)biphenyl-4-yl)-1,3,5-triazine (TBT-12), 2,4,6-tris(3'-(1H-indol-1-yl)biphenyl-4-yl)-1,3,5-triazine (TBT-13), 2,4,6-tris(3'-(2-phenyl-1H-benzo[d]imidazol-1-yl)biphenyl-4-yl)-1,3,5-triazine (TBT-14), a derivative or a similar group thereof.

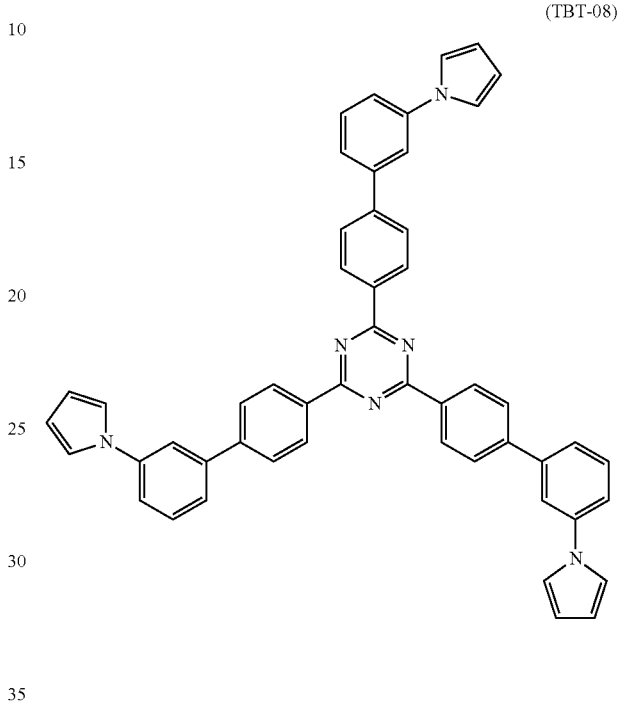
(TBT-08)

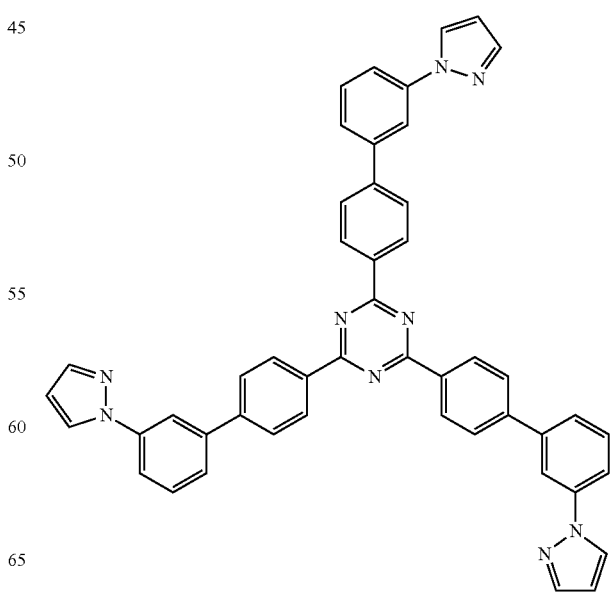
(TBT-09)

(TBT-10)
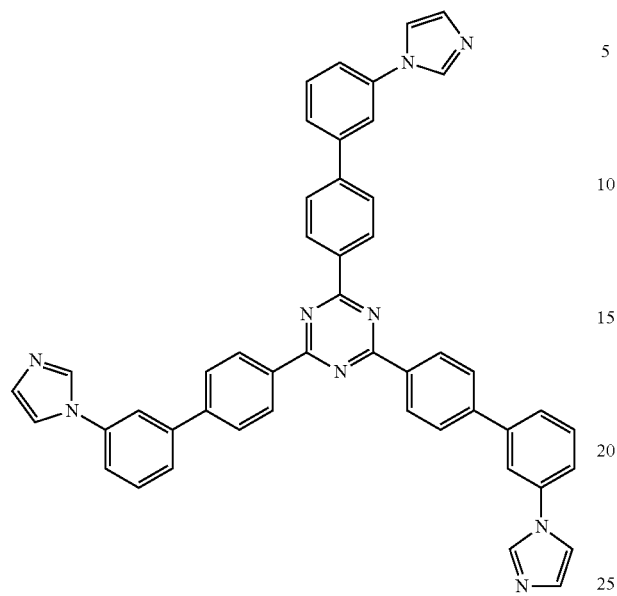
(TBT-11)
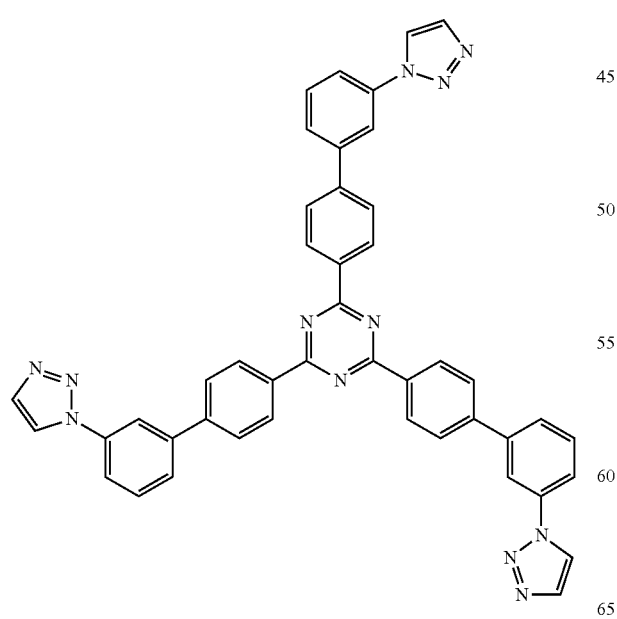
(TBT-12)
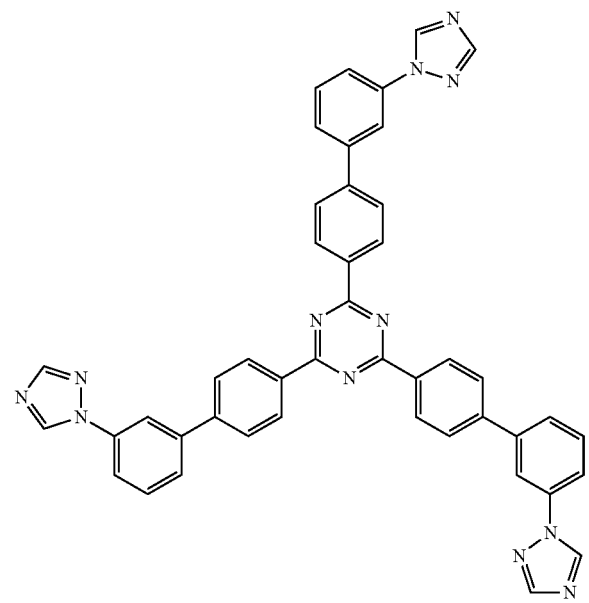
(TBT-13)
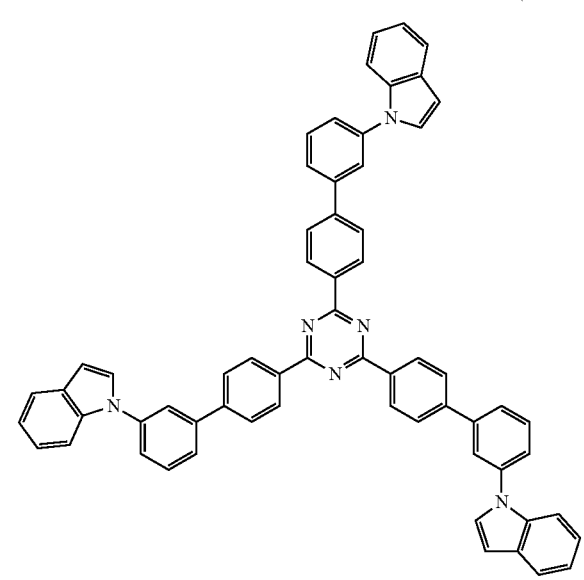

(TBT-14)

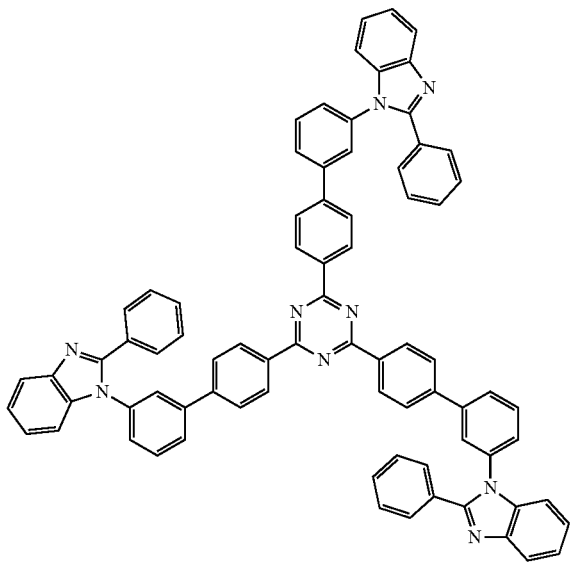

In the electron transport material, as the compound of the formula (1), the 1,3,5-triazine is used as a core molecule, so the compound keeps the high triplet state energy levels and good thermal stability. Moreover, compared with that the LUMO energy level of the existing 1,3,5-triazine derivative is between −1.9 eV and −2.3 eV, a nitrogen containing electron withdrawing group B is introduced at a meta-position of the group A of the compound of the formula (1), so that the compound of the formula (1) has a relatively low LUMO energy level, for example, between −2.6 eV and −3.0 eV. In such a manner, the energy barrier of injecting an electron can be reduced. Therefore, the electron transport material is applicable to an organic light emitting device.

The present invention provides another electron transport material, applicable to an organic light emitting device, and the electron transport material includes a compound represented by a formula (6) below:

(6)

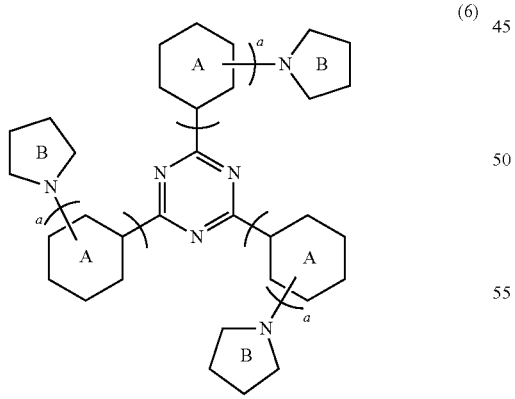

in which a group A represents an aromatic ring, a is 1, and a group B represents a nitrogen containing five-membered heterocyclic group and derivatives thereof, and has at least one nitrogen atom connected to a position other than the opposite position of the group A. In particular, for the compound of the formula (5), a 1,3,5-triazine is used as a core molecule, and positions 2,4,6 of the triazine are substituted by the group A.

A nitrogen containing group B is introduced at a position other than the opposite position of the group A. The position where the group A and the core structure 1,3,5-triazine are connected is used as a reference. The opposite position of the group A is the position opposite to the reference position. The positions other than the opposite position of the group A are the adjacent positions, meta-positions or other positions. For example, when the group A is a benzene ring, the group B is connected to the adjacent position or meta-position of the group A. When the group A is a naphthalene ring, the group B is connected a position other than a position 6 of the group A. In an embodiment, the manner that the group A and the group B are connected is, for example, bonding of a carbon-nitrogen bond.

In an embodiment, the group A is an aromatic ring, which may be a six-membered ring or another many-membered ring (for example, the five-membered ring), or a derivative thereof, for example, a fused ring, a bridge-fused ring, or have another substituent functional groups. In an embodiment, the group A represents, for example, a benzene ring, a fused benzene ring, a bridge-fused benzene ring, a derivative or a similar group thereof. In an embodiment, the group A represents, for example, a benzene ring, a naphthalene ring, a biphenyl ring, a derivative or a similar group thereof.

In an embodiment, the group B is, for example, an electron withdrawing group. In an embodiment, the group B is selected from the group consisting of:

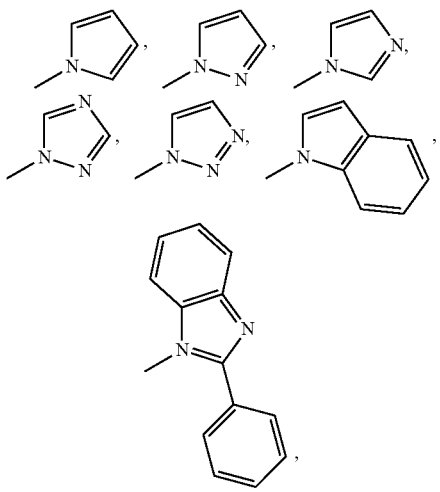

and derivatives and similar groups thereof.

In an embodiment, the group A represents, for example, a benzene ring. The group B is, for example, connected to a meta-position of the group A. An exemplary embodiment includes the compounds TPT01 to TPT07 and derivatives and similar groups thereof above. It should be noted that in other embodiments that the group A represents the benzene ring, the group B can be connected to adjacent positions of the group A. As the difference of the structures of the compounds and the compounds TPT01 to TPT07 is only that the group B is connected to the adjacent position of the benzene ring, and the structures can be easily inferred by persons of ordinary skill in the art with reference to the compounds TPT01 to TPT07, the drawing is omitted here.

In an embodiment, the group A represents, for example, a naphthalene ring. The group B is, for example, connected to positions 4, 5 or 7 of the group A, and the exemplary embodiment thereof includes the compounds TNT01 to TNT07 and derivatives and similar groups thereof above. It should be noted that in other embodiments that the group A represents the naphthalene ring, when a position 1 of the group A is connected to the core structure 1,3,5-triazine, the group B may be connected to a positions 3 or 6 of the group A. As the differences of the structures of the compounds and the compounds TNT01 to TNT07 are only that the position where the group A is connected to the core structure 1,3,5-triazine and the position where the group B is connected to the naphthalene ring, and the structures can be easily inferred by persons of ordinary skill in the art with reference to the compounds TNT01 to TNT07, the drawing is omitted here.

In an embodiment, the group A represents, for example, a biphenyl ring. When a position 3 of the group A is connected to core structure 1,3,5-triazine, the group B is, for example, connected to a position 4' of the group A. Alternatively, when a position 4 of the group A is connected to the core structure 1,3,5-triazine, the group B is, for example, connected to a position 3' of the group A, and the exemplary embodiment includes the compounds TBT01 to TBT14 and derivatives and similar groups thereof above. It should be noted that in other embodiments that the group A represents a biphenyl ring, when a position 4 of the group A is connected to the core structure 1,3,5-triazine, the group B may also be connected to a position 5' of the group A. As the difference of the structures of the compound and the compounds TBT01 to TBT14 is only the position where the group B is connected to the biphenyl ring, and the structures can be easily inferred by persons of ordinary skill in the art with reference to the compounds TBT01 to TBT14, the drawing is omitted here.

In the electron transport material, as in the compound of the formula (6), the 1,3,5-triazine is used as the core molecule, so the high triplet state energy level and good thermal stability are kept. Moreover, compared with that the LUMO energy level of the 1,3,5-triazine derivative is between −1.9 eV and −2.3 eV, a nitrogen containing electron withdrawing group B is introduced at a position other than a position opposite to the group A in the compound of the formula (6), so that the compound of the formula (6) has a relatively low LUMO energy level, for example, between −2.6 eV and −3.0 eV. In such a manner, the energy barrier of injecting an electron can be reduced. Therefore, the electron transport material is applicable to the organic light emitting device.

Subsequently, the organic light emitting device in which the compound of the formula (1) is used as the electron transport material is described.

Figure 1B:
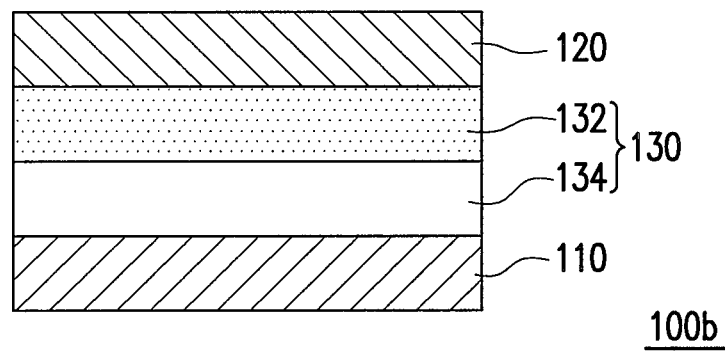
FIG. 1B is a schematic sectional view of an organic light emitting device according to an embodiment of the present invention.

FIG. 1A and FIG. 1B are schematic sectional views of an organic light emitting device according to two embodiments of the present invention. Referring to FIG. 1A and FIG. 1B, an organic light emitting device 100a or 100b includes a first electrode layer 110, a second electrode layer 120, and a light emitting material layer 130. In the embodiment in FIG. 1A, the light emitting material layer 130 is a light emitting material layer 130a. In the embodiment in FIG. 1B, the light emitting material layer 130 is a light emitting material layer 130b. The two embodiments illustrate the even mixing and the layering the electron transport material and the organic light emitting material, respectively.

The second electrode layer 120 is disposed opposite to the first electrode layer 110. The material of the first electrode layer 110 and the second electrode layer 120 can be a transparent conductive material, a semitransparent conductive material or an opaque conductive material. The first electrode layer 110 and the second electrode layer 120 may have a structure of a single layer or multiple layers. The transparent conductive material can include metal oxide such as indium tin oxide, indium zinc oxide, aluminum tin oxide, aluminum zinc oxide, indium germanium zinc oxide, or other suitable oxides (such as zinc oxide), or a stacked layer of at least two thereof. The opaque conductive material includes metal such as gold, silver, aluminum, molybdenum, copper, titanium, chrome, tungsten or other suitable metal. The semitransparent conductive material includes very thin metal, for example, a metal film with the thickness smaller than 500 nanometers, or a semitransparent material of low work functions. In this embodiment, the first electrode layer 110 is, for example, an anode, and the second electrode layer 120 is, for example, a cathode. However, it should be noted that, whether the first electrode 110 and the second electrode 120 are a cathode or an anode varies based on design demands.

The light emitting material layer 130 is disposed between the first electrode layer 110 and the second electrode layer 120, and includes an organic light emitting material and an electron transport material. The electron transport material includes a compound represented by a formula (1) below:

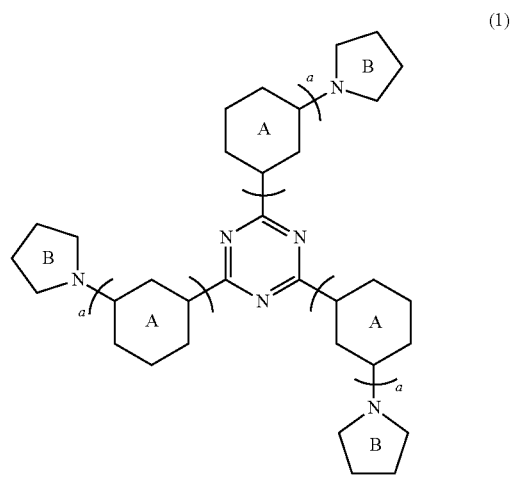

(1)

in which a group A represents an aromatic ring, a is 1, and a group B represents a nitrogen containing five-membered heterocyclic group and derivatives thereof, and has at least one nitrogen atom connected to a meta-position of the group A. The electron transport material can be referred to the description of the electron transport material including the compound of the formula (1) above, which is no longer described here.

In this embodiment, as shown in FIG. 1A and FIG. 1B, the electron transport material may be any one of the above electron transport materials including the compound of the formula (1). The LUMO energy level of the electron transport material is, for example, between −2.6 eV and −3.0 eV. The organic light emitting material may be a singlet-state excited-state fluorescent material, a triplet-state excited-state phosphorescent material or other suitable light emitting materials such as Ir(ppy)$_3$, Ir(ppy)$_2$(acac), and Ir(bt)$_2$(acac). As shown in FIG. 1A, the electron transport material 132a and the organic light emitting material 134a may be evenly mixed. The electron transport material 132a may serve as a light emitting host material, whereas the organic light emitting material 134a may also serve as a light emitting dopant material. In addition, a hole transport material may be further selectively added in the light emitting material layer 13a to enhance the luminous efficiency.

As shown in FIG. 1A, in the organic light emitting device 100a of the embodiment, the electron transport material 132a and the organic light emitting material 134a are, for example, evenly mixed to form a light emitting material layer 130a serving as an organic light emitting layer. For example, in the light emitting material layer 130a, the electron transport material 132a serves, for example, as a light emitting host material, and the organic light emitting material 134a evenly distributed in the electron transport material 132a by doping. The electron transport material 132a is in an amount of, for example, about 90%, and the organic light emitting material 134a is in an amount of, for example, about 10%. In this embodiment, the electron transport material 132a may be any one of the above electron transport materials including the compound of the formula (1), such as the electron transport material including the compound TPT02. The organic light emitting material 134a is, for example, Ir(ppy)$_3$, Ir(ppy)$_2$(acac), Ir(bt)$_2$(acac).

In another embodiment, as shown in FIG. 1B, the light emitting material layer 130b includes, for example, an ETL 132 and an organic light emitting layer 134, and the ETL 132 is disposed between the organic light emitting layer 134 and the second electrode layer 120. The ETL 132 is formed of an electron transport material. The organic light emitting layer 134 is formed of an organic light emitting material. In other words, in the organic light emitting device 100b, the electron transport material and the organic light emitting material are used to form the ETL 132 and the organic light emitting layer 134, respectively.

Figure 2:
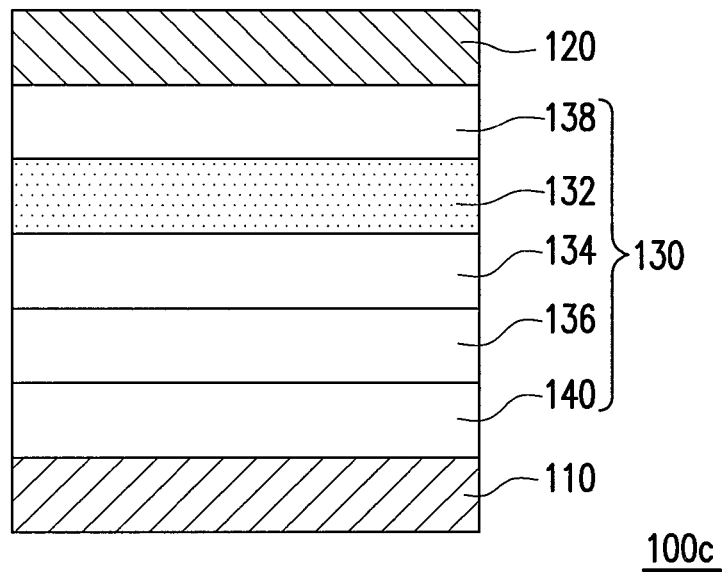
FIG. 2 is a schematic sectional view of an organic light emitting device according to an embodiment of the present invention.

In an embodiment, as shown in FIG. 2, the structure of the organic light emitting device 100c is similar to the structure of the organic light emitting device 100b shown in FIG. 1B. However, to further enhance the luminous efficiency of the organic light emitting device 100c, the hole transport layer 136 is further disposed, which is formed of the hole transport material. The hole transport layer 136 is, for example, disposed between the organic light emitting layer 134 and the first electrode layer 110. In addition, the light emitting material layer 130c may further include an electron inject layer 138 and a hole injection layer 140. The electron inject layer 138 is formed of an electron injection material and is, for example, disposed between the second electrode layer 120 and the ETL 132. The hole injection layer 140 is formed of a hole injection material and, is, for example, disposed between the first electrode layer 110 and the hole transport layer 136.

Figure 3:
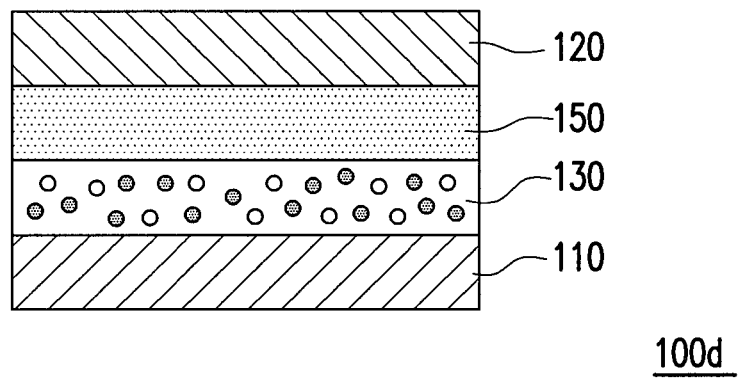
FIG. 3 is a schematic sectional view of an organic light emitting device according to an embodiment of the present invention.

In the embodiment as shown in FIG. 3, the structure of the organic light emitting device 100d is similar to the structure of the organic light emitting device 100a shown in FIG. 1A. However, to further enhance the luminous efficiency of the organic light emitting device 100d, in addition to the organic light emitting material layer 130d which is similar to the above organic light emitting material layer 130a, the organic light emitting device 100d may further include an ETL 150. The ETL 150 may be formed of any one of the above electron transport materials that includes the compound of the formula (1) (as shown in FIG. 3), or formed of a conventional electron transport material. In other words, the electron transport material that includes the compound of the formula (1) may be used as the light emitting host material in the light emitting material layer or may separately form the ETL.

In the organic light emitting device in the embodiment, the light emitting material layer uses the electron transport material that includes the compound of the formula (1). As the electron transport material that includes the compound of the formula (1) can provide a relatively low LUMO energy level, the energy barrier of injecting an electron can be reduced, so that the organic light emitting device has a desirable luminous efficiency.

Next, the synthesis methods of the compounds TPT-02, TPT-03, and TPT-06 are introduced through the experiments, and the characteristics of the compounds TPT-02, TPT-03, and TPT-06 are compound with that of the T2T. The compound TPT-02 is further used as the electron transport material of the organic light emitting device to compare the device characteristics of the organic light emitting device of the present invention and the conventional organic light emitting device.

[Synthesis of Compound TPT-02]

3-bromobenzonitrile (2 g, 10 mmol) is added in a 100-milliliter round-bottom flask and a stir bar is placed. Next, 20 ml CH$_2$Cl$_2$ is added in the round-bottom flask and trifluoromethanesulfonic acid (TfOH) (4 ml, 20 mmol) is added at the room temperature, which are then stirred for reaction for one day. After the reaction for one day, sodium bicarbonate (NaHCO$_3$) aqueous solution is added to quench the reaction. Next, CH$_2$Cl$_2$ is used to extract an organic layer of the resultant solution, which is then dried with the anhydrous magnesium sulfate. Subsequently, the resultant solution is filtered and the filtrate is then concentrated at reduced pressure. Next, the filtrate is precipitated by adding CH$_2$Cl$_2$ and hexane and filtered, to obtain an intermediate 1 in the form a white solid (1.21 g, 2.2 mmol, and purity of 66%). The reaction equation is as follows.

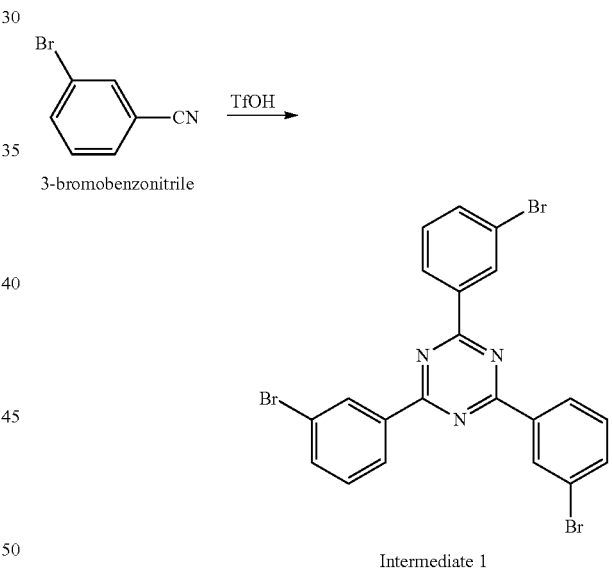

Intermediate 1

The intermediate 1 (2 g, 3.66 mmol), pyrazole (1.5 g, 21.97 mmol), copper iodide (CuI) (420 mg, 2.20 mmol), cesium carbonate (Cs$_2$CO$_3$) (7.16 g, 21.97 mmol) and a stir bar are placed in a 250 ml two-necked flask. Next, a condenser is erected, the condenser is vacuumed, argon is fed-in, and dimethylformamide (DMF) (60 ml) is injected by using a syringe. The solution is heated to 120° C., and stirred for reaction for 3 days. After the reaction is completed, the temperature of the solution is reduced to the room temperature, and DMF is removed therefrom. The solution is extracted by using the CHCl$_3$ to obtain an organic layer, and the organic layer is dried with the anhydrous magnesium sulfate. Subsequently, the resultant solution is filtered, and concentrated at reduced pressure, and then the solid is purified through Column Chromatography (CH$_2$Cl$_2$/Hexane/MeOH=5/2/0.1) to obtain a compound TPT-02 (1.02 g, 2.00 mmol, 55%) in the form of a gray white solid. The reaction equation is as follows.

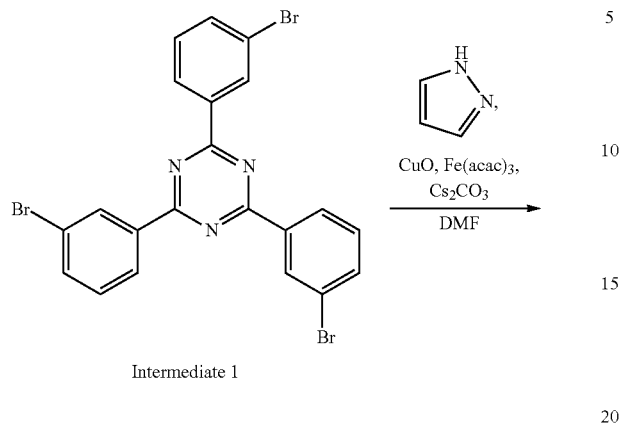

Intermediate 1

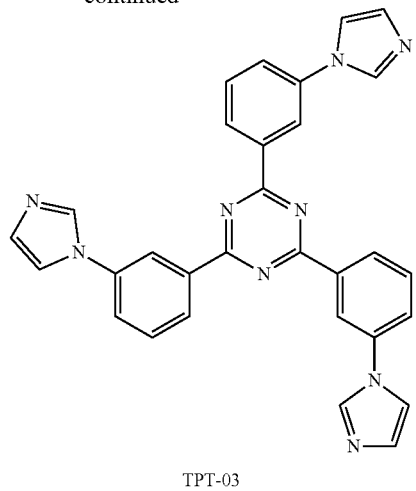

TPT-03

[Synthesis of Compound TPT-06]

The synthesis method of the compound TPT-06 is similar to the synthesis method of the compound TPT-02 except that the pyrazole is replaced with the indole. The reaction equation is as follows.

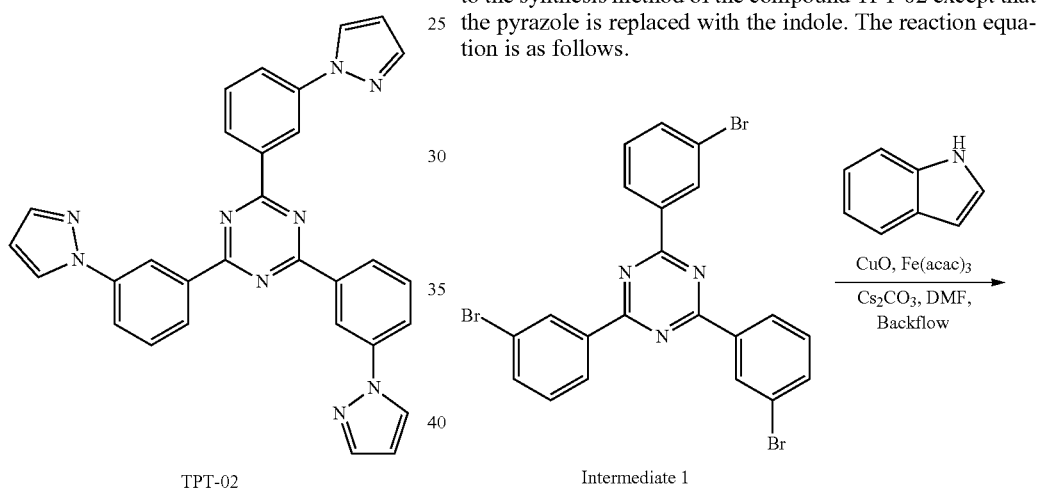

TPT-02

Intermediate 1

[Synthesis of Compound TPT-03]

The synthesis method of the compound TPT-03 is similar to the synthesis method of the compound TPT-02 except that the pyrazole is replaced with the imidazole. The reaction equation is as follows.

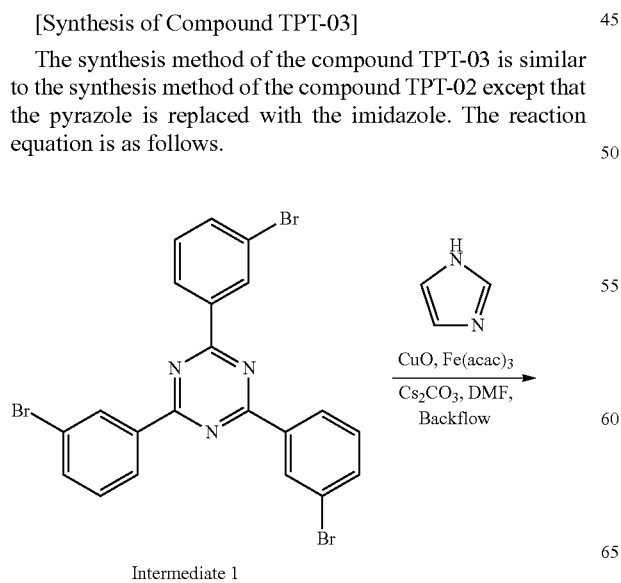

Intermediate 1

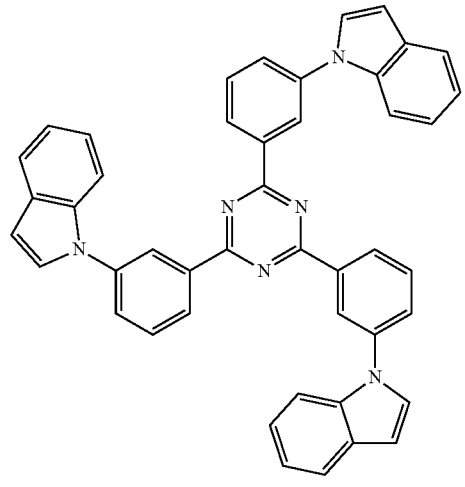

TPT-06

[Characteristics of Compounds TPT-02, TPT-03, and TPT-06]

As for the obtained compounds TPT-02, TPT-03, and TPT-06, the glass transition temperature Tg, the crystallization temperature $T_c$ and melting points $T_m$, the decomposition temperature $T_d$, triplet energy $E_T$ and energy levels/bandgap HOMO/LUMO/$E_g$ thereof are measured. The results are shown in Table 1.

TABLE 1

|  | $T_g/T_c/T_m$ (° C.) | $T_d$ (° C.) | $E_T$ (eV) | HOMO/LUMO/$E_g$ (eV) |
|---|---|---|---|---|
| T2T | 95/137/204 | 352 | 2.80 | −5.64/−2.08/3.56 |
| TPT-02 | −/−/− | 352 | 2.85 | −6.27/−2.72/3.55 |
| TPT-03 | −/−/− | 366 | 2.91 | −6.48/−2.86/3.62 |
| TPT-06 | −/−/− | 394 | 2.91 | −6.61/−2.69/3.92 |

As seen from Table 1, compared with the comparative example, the compound 2,4,6-tris(biphenyl-3-yl)-1,3,5-triazine (T2T), the compounds TPT-02, TPT-03, and TPT-06 of the present invention not only have good thermal stability and high triplet state energy level, but also has a relatively low HOMO/LUMO energy level, in which the LUMO energy level is between −2.7 eV and −3.0 eV.

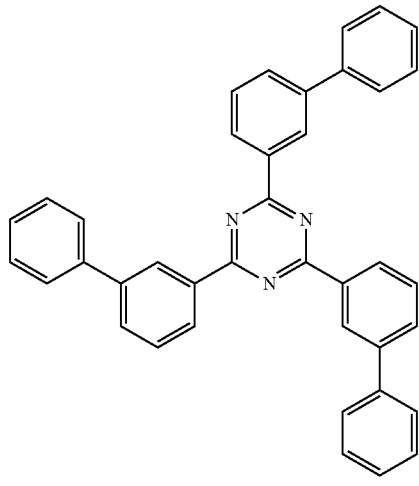

T2T

[Compound TPT-02 Used as Electron Transport Material of Organic Light Emitting Device]

The organic light emitting devices of an experimental example 1 and a comparative example 1 and the organic light emitting devices of experimental examples 2-1, 2-2, and 2-3 and a comparative example 2 are fabricated, respectively.

The organic light emitting device of the experimental example 1 includes an anode, a hole injection layer, a hole transport layer, an organic light emitting layer, an ETL, an auxiliary material layer, and a cathode stacked in sequence. The anode is indium tin oxide. The hole injection layer is 20 nm of the Poly(3,4-ethylenedioxythiophene):poly(styrenesulfonate) (PEDOT:PSS). The hole transport layer is 20 nm of the NPB (N,N'-bis(1-naphthyl)-N,N'-diphenyl-1,1'-biphenyl-4,4'diamine) and 5 nm of 4,4',4''-tris(carbazol-9-yl)triphenylamine (TCTA). The organic light emitting layer is 25 nm and includes 90% of the compound TPT-02 as the light emitting host material and 10% of Ir(ppy)$_2$(acac) as dopants. The ETL is 50 nm and includes the compound TPT-02 as the ETL material. The auxiliary material layer is 1 nm of LiF layer. The cathode is aluminum.

The difference between the organic light emitting device of the comparative example 1 and the organic light emitting device of the experimental example 1 is only that the conventional compound T2T replaces the compound TPT-02 in the organic light emitting layer and the ETL as the light emitting host material.

For the device characteristic test of the organic light emitting devices in the experimental example 1 and the comparative example 1, the results are shown in Table 2.

TABLE 2

| Group (Light Emitting Host Material) | Von [V] | L 1000 nit [V, %] | $L_{max}$ [cd/m$^2$] | $I_{max}$ [mA/cm$^2$] | $h_{ext, max}$ %, cd/A | $h_{p, max}$ lm/W | CIE (x; y) |
|---|---|---|---|---|---|---|---|
| Comparative Example 1 (T2T) | 2 | 10.5, 8.5% | 49,500 (18 V) | 630 | 9.7%, 36.3 (L = 100 nit) | 14.7 | 0.32; 0.64 |
| Experimental Example 1 (TPT-02) | 2 | 4.1, 15% | 103,700 (9.5 V) | 1680 | 15.7%, 56.6 (L = 170 nit) | 71.6 | 0.35; 0.61 |

As can be seen from Table 2, at the luminance of 1000 cd/m$^2$, compared with the organic light emitting device that uses the conventional compound T2T as the light emitting host material and the ETL of the organic light emitting layer, the operating voltage of the organic light emitting device that uses the compound TPT-02 of the present invention as the organic light emitting layer and the ETL is 4.1 V, which is much smaller than the 10.5 V of the organic light emitting device that uses the conventional compound T2T. In addition, at the luminance of 1000 cd/m$^2$, the external quantum efficiency of the organic light emitting device that uses the compound TPT-02 of the present invention is 15%, which is also better than the 8.5% of the organic light emitting device that uses the conventional compound T2T. In other words, the organic light emitting device that uses the compound TPT-02 of the present invention as the organic light emitting layer and the ETL has a desirable luminous efficiency.

The organic light emitting devices of the experimental examples 2-1, 2-2, and 2-3 include an anode, a hole injection layer, a hole transport layer, an organic light emitting layer, an ETL, an auxiliary material layer, and a cathode stacked in sequence. The anode is indium tin oxide. The hole injection layer is 60 nm of 1,4,5,8,9,11-hexaazatriphenylene-hexacarbonitrile (HAT-CN). The hole transport layer is 30 nm of 1,1-bis[N,N-di(p-tolyl)aminophenyl]cyclohexane (TAPC). The organic light emitting layer is 10 nm and includes 90% of 4,4'-bis(N-carbazolyl)biphenyl (CBP) as the light emitting host material and 10% of the light emitting material as dopants. The ETL is 50 nm of the compound TPT-02. The auxiliary material layer is 1 nm of lithium fluoride (LiF). The cathode is aluminum. The light emitting dopant materials doped in the light emitting host materials in the experimental examples 2-1, 2-2, and 2-3 are Ir(ppy)$_3$, Ir(ppy)$_2$(acac), and Ir(bt)$_2$(acac), respectively.

The device characteristic test is performed on the organic light emitting devices in the experimental examples 2-1, 2-2, and 2-3, and the results are shown in Table 3.

TABLE 3

| Group | at 2 mA/cm$^2$ | | | |
|---|---|---|---|---|
| | Voltage (V) | Current Efficiency (cd/A) | External Quantum Efficiency (%) | CIEx,y |
| Experimental Example 2-1 | 6.1 | 31.1 | 9.4 | 0.307, 0.619 |
| Experimental Example 2-2 | 5.8 | 31.9 | 8.8 | 0.332, 0.623 |
| Experimental Example 2-3 | 5.4 | 18.5 | 6.8 | 0.507, 0.487 |

As seen from Table 3, the organic light emitting device that uses the compound TPT-02 of the present invention as the ETL has the desirable luminous efficiency.

In light of the foregoing, the electron transport material of the present invention includes the compound of the formula (1). The compound of the formula (1) uses the 1,3,5-triazine as the core molecule and a nitrogen containing electron withdrawing group B is introduced at a meta-position of the group A. Therefore, the compound of the formula (1) keeps the high triplet state energy level and good thermal stability of the 1,3,5-triazine and has a relatively low LUMO energy level, for example, between −2.6 eV and −3.0 eV, thereby further reducing the energy barrier of injecting an electron. Therefore, the organic light emitting device that uses the electron transport material of the present invention has a desirable luminous efficiency.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An organic light emitting device, comprising:
   a first electrode layer;
   a second electrode layer, disposed opposite to the first electrode layer; and
   a light emitting material layer, disposed between the first electrode layer and the second electrode layer, and comprising an organic light emitting material and an electron transport material, wherein the electron transport material comprises a compound represented by a formula (1) below:

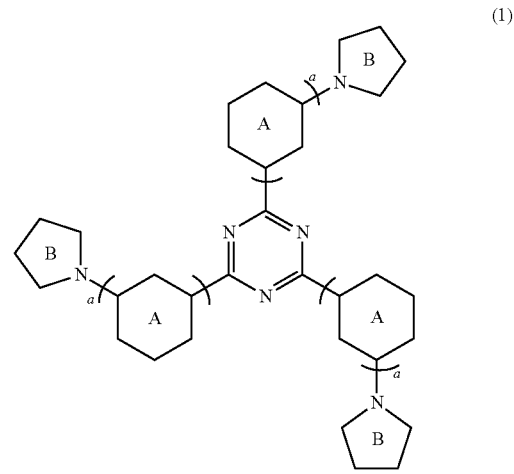

(1)

wherein a group A represents an unsubstituted biphenyl ring, a is 1, and a group B represents a nitrogen containing five-membered heterocyclic group and derivatives thereof, and comprises at least one nitrogen atom connected to a meta-position of the group A, and wherein the group B is selected from the group consisting of:

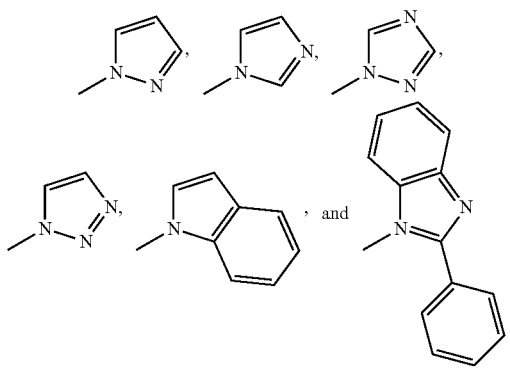

2. The organic light emitting device according to claim 1, wherein the electron transport material comprises a compound represented by a formula (4) below:

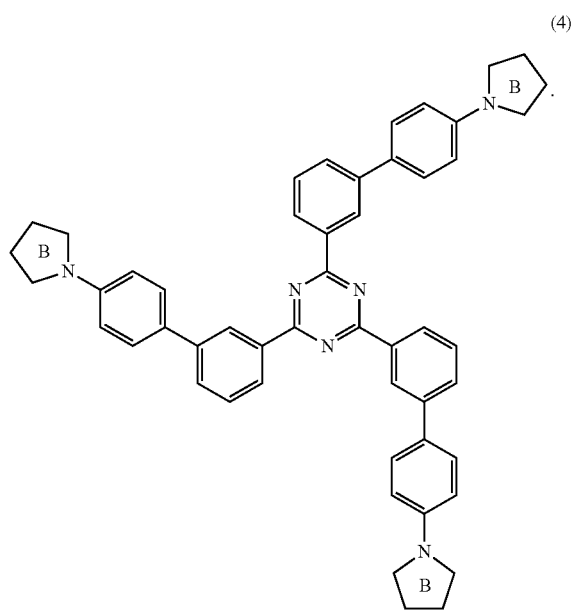

(4)

3. The organic light emitting device according to claim 1, wherein the electron transport material comprises a compound represented by a formula (5) below:

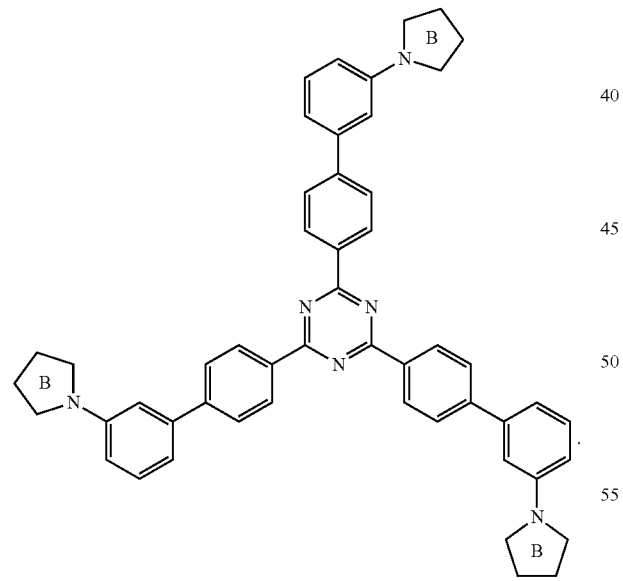

(5)

4. The organic light emitting device according to claim 1, wherein a lowest unoccupied molecular orbital (LUMO) energy level of the electron transport material is between −2.6 eV and −3.0 eV.

5. The organic light emitting device according to claim 1, wherein the electron transport material and the organic light emitting material are evenly mixed.

6. The organic light emitting device according to claim 5, wherein the electron transport material comprises a light emitting host material, and the organic light emitting material comprises a light emitting dopant material.

7. The organic light emitting device according to claim 1, wherein the light emitting material layer further comprises a hole transport material, and the hole transport material and the electron transport material and the organic light emitting material are evenly mixed.

8. The organic light emitting device according to claim 1, wherein the light emitting material layer comprises an electron transport layer (ETL) and an organic light emitting layer, the ETL is disposed between the organic light emitting layer and the second electrode layer, the ETL is formed of the electron transport material, and the organic light emitting layer is formed of the organic light emitting material.

9. The organic light emitting device according to claim 1, further comprising a hole transport layer, located between the first electrode layer and the light emitting material layer.

10. An electron transport material, applicable to an organic light emitting device, the electron transport material comprising:
  a compound represented by a formula (1) below:

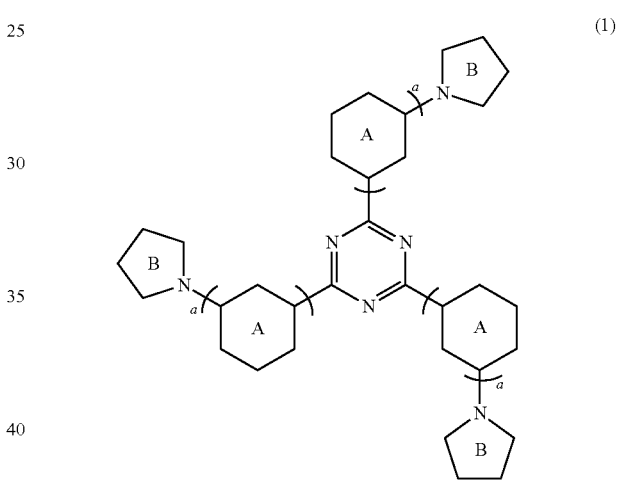

(1)

wherein a group A represents an unsubstituted biphenyl ring, a is 1, and a group B represents a nitrogen containing five-membered heterocyclic group and derivatives thereof, and comprises at least one nitrogen atom connected to a meta-position of the group A, and wherein the group B is selected from the group consisting of:

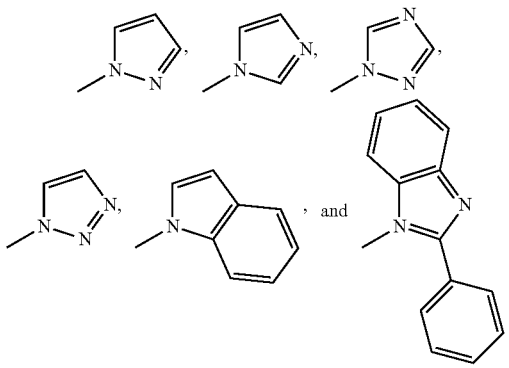

11. The electron transport material according to claim 10, wherein the electron transport material comprises a compound represented by a formula (4) below:

(4)

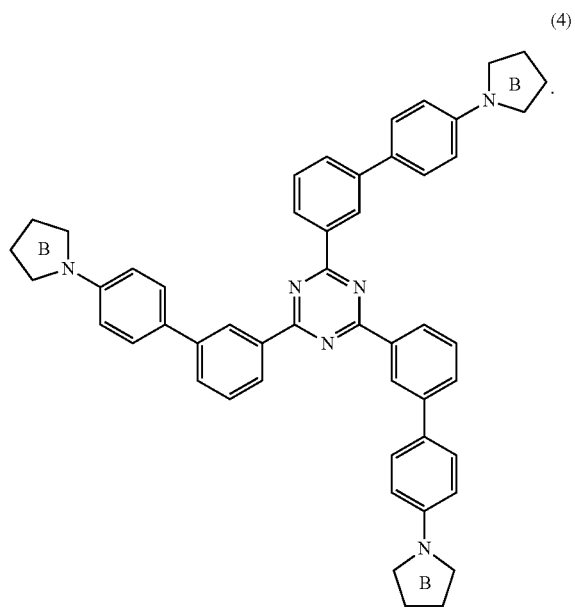

12. The electron transport material according to claim 10, wherein the electron transport material comprises a compound represented by a formula (5) below:

(5)

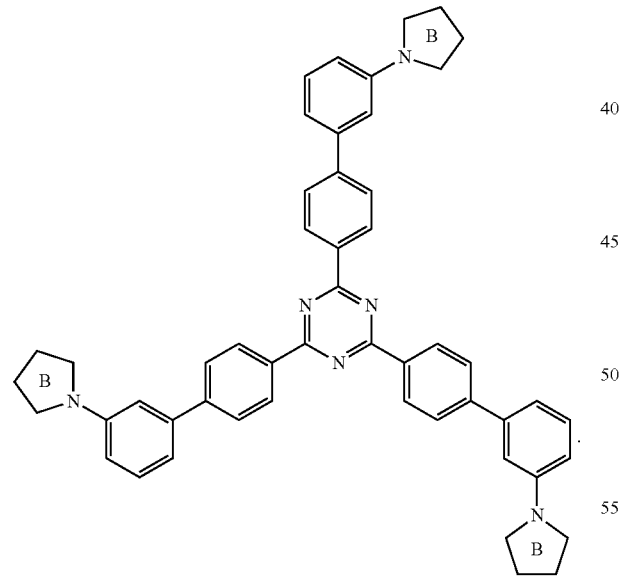

13. The electron transport material according to claim 10, wherein a lowest unoccupied molecular orbital (LUMO) energy level of the electron transport material is between −2.6 eV and −3.0 eV.

14. An electron transport material, applicable to an organic light emitting device, the electron transport material comprising:

a compound represented by a formula (6) below:

(6)

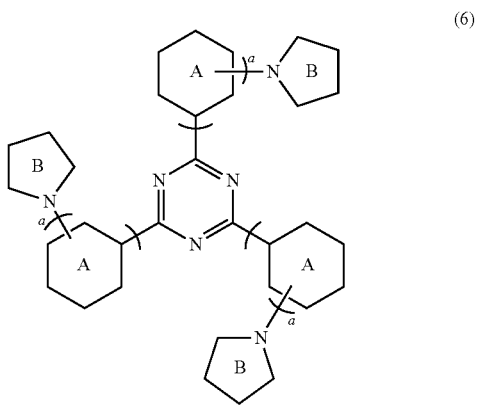

wherein a group A represents an unsubstituted biphenyl ring, a is 1, and a group B represents a nitrogen containing five-membered heterocyclic group and derivatives thereof, and comprises at least one nitrogen atom connected to a position other than the opposite position of the group A, and wherein the group B is selected from the group consisting of:

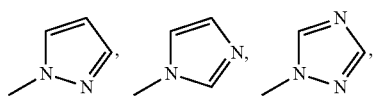

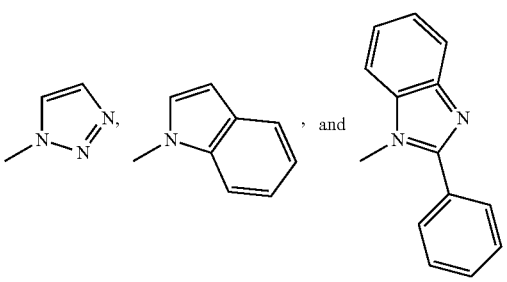

* * * * *